United States Patent
Bernd et al.

(10) Patent No.: US 7,732,412 B2
(45) Date of Patent: *Jun. 8, 2010

(54) METHODS OF TREATMENT USING NOVEL LHRH ANTAGONISTS HAVING IMPROVED SOLUBILITY PROPERTIES

(75) Inventors: Michael Bernd, Frankfurt (DE); Bernhard Kutscher, Maintal (DE); Eckhard Gunther, Maintal (DE); Peter Romeis, Gelnhausen (DE); Thomas Reissmann, Frankfurt (DE); Thomas Beckers, Constance (DE)

(73) Assignee: Zentaris GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/459,583

(22) Filed: Jul. 24, 2006

(65) Prior Publication Data

US 2006/0281685 A1    Dec. 14, 2006

Related U.S. Application Data

(60) Continuation-in-part of application No. 10/671,573, filed on Sep. 29, 2003, now Pat. No. 7,148,195, which is a division of application No. 09/525,007, filed on Mar. 14, 2000, now Pat. No. 6,627,609.

(30) Foreign Application Priority Data

Mar. 17, 1999    (DE) .............................. 199 00 771

(51) Int. Cl.
    *A61K 38/00*    (2006.01)
(52) U.S. Cl. ......................................... 514/15; 530/328
(58) Field of Classification Search ........................ None
    See application file for complete search history.

(56) References Cited

U.S. PATENT DOCUMENTS

| 4,581,169 A | 4/1986 | Nestor et al. |
| 4,628,044 A | 12/1986 | Loozen |
| 5,198,533 A | 3/1993 | Schally et al. |
| 5,300,492 A | 4/1994 | Haviv et al. |
| 5,527,777 A | 6/1996 | Thamm et al. |
| 5,942,493 A | 8/1999 | Kutscher et al. |
| 6,054,432 A * | 4/2000 | Engel et al. ................... 514/15 |
| 6,586,403 B1 * | 7/2003 | Mathison et al. .............. 514/18 |
| 2004/0259801 A1 * | 12/2004 | Damm et al. ................. 514/15 |

FOREIGN PATENT DOCUMENTS

| DE | 195 44 212 A1 | 6/1997 |
| EP | 0 328 090 A1 | 8/1989 |
| EP | 0 413 209 A1 | 2/1991 |
| EP | 0417454 | 3/1991 |
| WO | WO 97/19953 | 6/1997 |
| WO | WO 98/25642 | 6/1998 |
| WO | WO 00/55190 | 9/2000 |

OTHER PUBLICATIONS

Engel JB et al., New peptidic GnRH antagonists offer a broad range of therapeutic applications, 2005, Letters in Drug Design and Discovery, 2:533-536.*
Registry information for Ozarelix, 1 page.*
Haviv et al., "The Effect of NmeTyr$^5$ Substitution in Luteinizing Hormone-Releasing Hormone Antagonists", *J. Med. Chem.*, 1993, vol. 36, No. 7, pp. 928-933.
Dermer, Another Anniversary for the War on Cancer, *Bio/Technology*, 1994, vol. 12, p. 320.
Palatsi et al., "Pituitary function and DHEA-S in male acne and DHEA-S, prolactin and cortisol before and after oral contraceptive treatment in female acne," Acta. Derma. Venerol., 66:225-30 (1986) (abstract only).

* cited by examiner

*Primary Examiner*—Anish Gupta
*Assistant Examiner*—Ronald T Niebauer
(74) *Attorney, Agent, or Firm*—Pillsbury Winthrop Shaw Pittman LLP

(57) ABSTRACT

The invention relates to peptides which contain N-methylated amino acid units and have improved water solubility. The invention also relates methods for treating a hormone-dependent tumor or a non-malignant indication that is treatable by LH-RH suppression, the method comprising administering to a patient in need of the treatment a therapeutically effective amount of a compound of the invention. Hormone-dependent cancers that can be treated with the methods of the invention include prostate cancer, breast cancer, ovarian cancer, endometrial cancer, and pancreatic cancer. Non-malignant indications which can be treated by the methods of the invention include benign prostate hyperplasia (BPH), endometriosis, acne, polycystic ovarian disease, dysmenorrhea, precocious puberty, and uterine fibroids and other leiomyomas.

8 Claims, No Drawings

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: LH-RH: Gonadorelin

<400> SEQUENCE: 1

Glu His Trp Ser Tyr Gly Leu Arg Pro Gly
1               5                   10
```

METHODS OF TREATMENT USING NOVEL LHRH ANTAGONISTS HAVING IMPROVED SOLUBILITY PROPERTIES

CROSS REFERENCE TO RELATED APPLICATIONS

This is a continuation-in-part of U.S. patent application Ser. No. 10/671,573, filed Sep. 29, 2003, now U.S. Pat. No. 7,148,195 which is a divisional of U.S. patent application Ser. No. 09/525,007, filed Mar. 14, 2000, now U.S. Pat. No. 6,627,609 B1, which in turn claims priority to German Patent Application No. 199 11 771.3, filed Mar. 17, 1999, which applications are all incorporated herein in their entirety by reference.

BACKGROUND OF THE INVENTION

1. Field of the Invention

The invention relates to antagonists of luteinizing hormone-releasing hormone (LH-RH) having improved solubility properties, processes for the preparation of these compounds, medicaments in which these compounds are contained, and therapeutic methods comprising administering the medicaments for the treatment of hormone-dependent tumors such as prostate cancer and ovarian cancer, and hormone-influenced non-malignant disorders such as benign prostate hyperplasia (BPH) and endometriosis.

2. Background Information

LH-RH, also referred to as gonadotropin-releasing hormone (GnRH), stimulates the pituitary secretion of both luteinizing hormone (LH) and follicle-stimulating hormone (FSH), which control the hormonal and reproductive functions of the gonads. LH-RH antagonists such as the peptide compounds of the present invention selectively block the secretion of LH and FSH by the pituitary gland, and are therapeutically useful in clinical situations in which the suppression of sexual steroids (testicular androgens and ovarian estrogens) is desired; for example, in the treatment of hormone-dependent tumors such as prostate cancer, breast cancer, ovarian cancer, and endometrial cancer, and in the treatment of hormone-influenced non-malignant disorders that are treatable by LH-RH suppression, such as BPH, endometriosis, and uterine fibroids and other leiomyomas. LH-RH receptors are also present on the surfaces of cancerous cells of hormone-dependent tumors (e.g., ovarian cancer) and appear to be involved in signaling pathways that promote proliferation of the cancer cells. Peptide LH-RH antagonists block the activity of these LH-RH receptors and inhibit cancer cell proliferation. Peptide LH-RH antagonists have been shown to be therapeutically effective in clinical use, and to have acceptable pharmacokinetic, safety and commercial profiles.

The nomenclature used for the definition of the peptides disclosed herein agrees with that nomenclature explained by the IUPAC-IUB Commission on Biochemical Nomenclature (European J. Biochem. 1984, 138, 9-37), in which, in agreement with the conventional representation, the amino groups at the N terminus appear to the left and the carboxyl group at the C terminus appears to the right. The LH-RH antagonists such as the peptides according to the invention include naturally occurring and synthetic amino acids, the former including Ala, Val, Leu, Ile, Ser, Thr, Lys, Arg, Asp, Asn, Glu, Gln, Cys, Met, Phe, Tyr, Pro, Trp and His. The abbreviations for the individual amino acid residues are based on the trivial names of the amino acids and are Ala=alanine, Arg=arginine, Gly=glycine, Leu=leucine, Lys=lysine, Pal (3)=3-(3-pyridyl) alanine, Nal(2)=3-(2-naphthyl)-alanine, Phe=phenylalanine, Cpa=4-chlorophenylalanine, Pro=proline, Ser=serine, Thr=threonine, Trp=tryptophan, Try=tyrosine and Sar=sarcosine. All amino acids described here originate from the L series, if not mentioned otherwise. For example, D-Nal (2) is the abbreviation for 3-(2-naphthyl)-D-alanine and Ser is the abbreviation for L-serine. Substitutions on the ε amino group in the side chain of lysine are represented by a term placed in brackets behind Lys, if appropriate in the form of an abbreviation.

Other abbreviations used are:

| | |
|---|---|
| Ac | Acetyl |
| Atz | 3-Amino-1,2,4-triazole-5-carbonyl |
| B | 4-(4-Amidinophenyl)amino-1,4-dioxobutyl |
| Boc | tert-Butyloxycarbonyl |
| Bop | Benzotriazol-1-oxy-tris (dimethylamino)-phosphonium hexafluorophosphate |
| DCC | Dicyclohexylcarbodiimide |
| DCM | Dichloromethane |
| Ddz | Dimethoxyphenyl-dimethylmethylenoxy-carbonyl (Dimethoxy-dimethyl-Z) |
| DIC | Diisopropylcarbodiimide |
| DIPEA | N,N-Diisopropylethylamine |
| DMF | Dimethylformamide |
| Fmoc | Fluorenylmethyloxycarbonyl |
| Hci | Homocitrulline |
| HF | Hydrofluoric acid |
| HOBt | 1-Hydroxybenzotriazole |
| HPLC | High-pressure liquid chromatography |
| Me | Methyl |
| TFA | Trifluoroacetic acid |
| Z | Benzyloxycarbonyl |

The peptides according to the invention are analogues of the luteinizing-hormone-releasing hormone (LH-RH), which has the following structure:

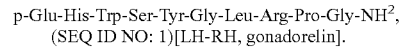

(SEQ ID NO: 1)[LH-RH, gonadorelin].

For more than 20 years, researchers have sought selective potent antagonists of the LH-RH decapeptide [M. Karten and J. E. Rivier, Endocrine Reviews 7, 44-66 (1986)] The high interest in such antagonists is based on their usefulness in the field of endocrinology, gynaecology, contraception and cancer. A large number of compounds have been prepared as potential LH-RH antagonists. The most interesting compounds which have been found to date are those compounds whose structures are a modification of the LH-RH structure.

The first series of potent antagonists was obtained by the introduction of aromatic amino acid residues into the positions 1, 2, 3 and 6 or 2, 3 and 6. The customary way of writing the compounds is as follows: the amino acids are first indicated which have taken the place of the amino acids originally present in the peptide chain of LH-RH, the positions in which the exchange took place being marked by superscripted figures. Furthermore, by the notation "LH-RH" placed afterwards it is expressed that these are LH-RH analogues in which the exchange has taken place.

Known antagonists are:

[Ac-D-Cpa$^{1,2}$, D-Trp$^{3,6}$] LH-RH (D. H. Coy et al., In: Gross, E. and Meienhofer, J. (Eds) Peptides; Proceedings of the 6th American Peptide Symposium, pp. 775-779, Pierce Chem. Co., Rockville III. (1979): [Ac-Pro$^1$, D-Cpa$^2$, D-Nal (2)$^{3,6}$] LH-RH (U.S. Pat. No. 4,419,347) and [Ac-Pro$^1$, D-Cpa$^2$, D-Trp$^{3,6}$] LH-RH (J. L. Pineda, et al., J. Clin. Endocrinol. Metab. 56, 420, 1983).

In order to improve the action of antagonists, basic amino acids, for example D-Arg, were later introduced into the 6 position. For example [Ac-D-Cpa$^{1,2}$, D-Trp$^3$, D-Arg$^6$, D-Ala$^{10}$] LH-RH (ORG-30276) (D. H. Coy, et al., Endocrinology 100, 1445, 1982); and [Ac-D-Nal(2)$^1$, D-Phe(4-F)$^2$, D-Trp$^3$, D-Arg$^6$] LH-RH (ORF 18260) (J. E. Rivier et al., in: Vickery B. H. Nestor, Jr. J. J., Hafez, E. S. E (Eds). LHRH and its Analogs, pp. 11-22 MTP Press, Lancaster, UK 1984).

Further potent LH-RH antagonists are described in WO 92/19651, WO 94/19370, WO 92/17025, WO 94/14841, WO 94/13313, EP 0 413 209 A1 and DE 195 44 212 A1, and U.S. Pat. Nos. 5,300,492, and 5,140,009. Peptide LH-RH antagonists are also described in U.S. Pat. Nos. 4,268,044, 4,581,169, 5,527,777, 5,198,533, and 5,942,493, and in WO 97/19953, WO 98/25642, WO 00/55190, EP 0 328 090 A2, and EP 0 413 209 A1.

The latter discloses compounds having a modified ornithine or lysine unit in position 6 and which correspond to the following formula:

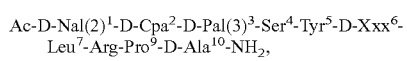
Ac-D-Nal(2)$^1$-D-Cpa$^2$-D-Pal(3)$^3$-Ser$^4$-Tyr$^5$-D-Xxx$^6$-Leu$^7$-Arg-Pro$^9$-D-Ala$^{10}$-NH$_2$, in which D-Xxx is an amino acid group of the general formula VI

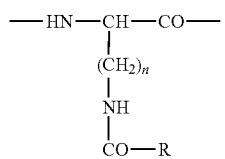

Further known LH-RH antagonists are antarelix, ganirelix and cetrorelix.

Antarelix:

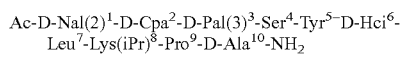
Ac-D-Nal(2)$^1$-D-Cpa$^2$-D-Pal(3)$^3$-Ser$^4$-Tyr$^5$-D-Hci$^6$-Leu$^7$-Lys(iPr)$^8$-Pro$^9$-D-Ala$^{10}$-NH$_2$ Ganirelix:

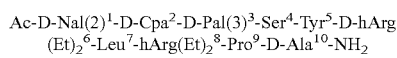
Ac-D-Nal(2)$^1$-D-Cpa$^2$-D-Pal(3)$^3$-Ser$^4$-Tyr$^5$-D-hArg(Et)$_2$$^6$-Leu$^7$-hArg(Et)$_2$$^8$-Pro$^9$-D-Ala$^{10}$-NH$_2$ Cetrorelix:

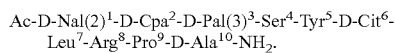
Ac-D-Nal(2)$^1$-D-Cpa$^2$-D-Pal(3)$^3$-Ser$^4$-Tyr$^5$-D-Cit$^6$-Leu$^7$-Arg$^8$-Pro$^9$-D-Ala$^{10}$-NH$_2$.

SUMMARY OF THE INVENTION

An object of the invention is to create novel LH-RH antagonists which have an increased enzymatic stability and significantly improved water solubility.

This object is achieved by compounds of the following general formula I

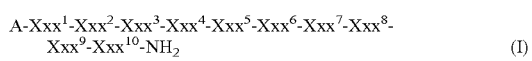
A-Xxx$^1$-Xxx$^2$-Xxx$^3$-Xxx$^4$-Xxx$^5$-Xxx$^6$-Xxx$^7$-Xxx$^8$-Xxx$^9$-Xxx$^{10}$-NH$_2$ (I)

in which

A is an acetyl or a 3-(4-fluorophenyl)propionyl group,

Xxx$^1$ is D-Nal(1) or D-Nal(2),

Xxx2-Xxx3 is D-Cpa-D-Pal(3) or a single bond,

XXx$^4$ is Ser,

Xxx$^5$ is N-Me-Tyr,

Xxx$^6$ is D-Cit, D-Hci or a D-amino acid group of the general formula II

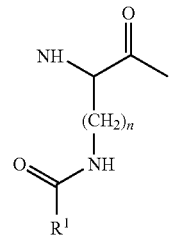

in which n is the number 3 or 4, where R$^1$ is a group having the general formula III

—(CH$_2$)$_p$—CO—NR$^2$R$^3$ (III)

where p is an integer from 1 to 4, R$^2$ is hydrogen or an alkyl group and R$^3$ is an unsubstituted or substituted aryl group or heteroaryl group, or R$^1$ is a 3-amino-1,2,4-triazole-5-carbonyl group or R$^1$ is a ring of the general formula IV

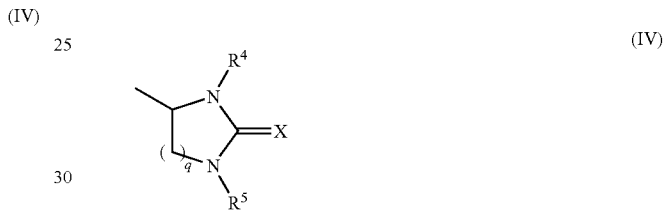

in which q is the number 1 or 2, R$^4$ is a hydrogen atom or an alkyl group, R$^5$ is a hydrogen atom or an alkyl group and X is an oxygen or sulphur atom, Xxx$^7$ is Leu or Nle, Xxx$^8$ is Arg or Lys (iPr), Xxx$^9$ is Pro and Xxx$^{10}$ is Ala, D-Ala or Sar, and their salts with pharmaceutically acceptable acids, in particular the acetates, embonates and trifluoroacetates.

Representative compounds according to the invention include compounds as described above, in which Xxx$^6$ is D-[ε-N'-(imidazolidin-2-on-4-yl) formyl]-Lys, D-(3-amino-1,2,4-triazole-3-carbonyl)-Lys, abbreviated D-Lys(Atz) or D-[ε-N'-4-(4-Amidinophenyl)-amino-1,4-dioxo-butyl]-Lys, abbreviated D-Lys(B).

Additional examples of compounds according to the invention are:

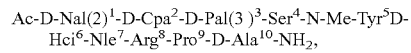
Ac-D-Nal(2)$^1$-D-Cpa$^2$-D-Pal(3 )$^3$-Ser$^4$-N-Me-Tyr$^5$D-Hci$^6$-Nle$^7$-Arg$^8$-Pro$^9$-D-Ala$^{10}$-NH$_2$,

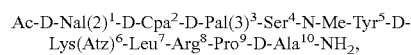
Ac-D-Nal(2)$^1$-D-Cpa$^2$-D-Pal(3)$^3$-Ser$^4$-N-Me-Tyr$^5$-D-Lys(Atz)$^6$-Leu$^7$-Arg$^8$-Pro$^9$-D-Ala$^{10}$-NH$_2$,

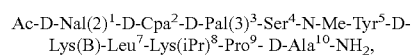
Ac-D-Nal(2)$^1$-D-Cpa$^2$-D-Pal(3)$^3$-Ser$^4$-N-Me-Tyr$^5$-D-Lys(B)-Leu$^7$-Lys(iPr)$^8$-Pro$^9$- D-Ala$^{10}$-NH$_2$,

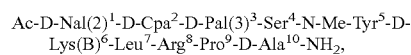
Ac-D-Nal(2)$^1$-D-Cpa$^2$-D-Pal(3)$^3$-Ser$^4$-N-Me-Tyr$^5$-D-Lys(B)$^6$-Leu$^7$-Arg$^8$-Pro$^9$-D-Ala$^{10}$-NH$_2$,

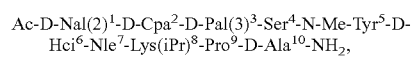
Ac-D-Nal(2)$^1$-D-Cpa$^2$-D-Pal(3)$^3$-Ser$^4$-N-Me-Tyr$^5$-D-Hci$^6$-Nle$^7$-Lys(iPr)$^8$-Pro$^9$-D-Ala$^{10}$-NH$_2$,

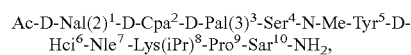
Ac-D-Nal(2)$^1$-D-Cpa$^2$-D-Pal(3)$^3$-Ser$^4$-N-Me-Tyr$^5$-D-Hci$^6$-Nle$^7$ -Lys(iPr)$^8$-Pro$^9$-Sar$^{10}$-NH$_2$, Ac-D-Nal(2)$^1$-D-Cpa$^2$-D-Pal(3)$^3$-Ser$^4$-N-Me-Tyr$^5$-D-Hci$^6$-Nle$^7$-Ar$^9$-Pro$^9$-Sar$^{10}$-NH$_2$, 3-(4-Fluorophenyl)propionyl-D-Nal(1)$^1$-Ser$^4$-N-Me-Tyr$^5$-D -Lys(Atz)$^6$-Leu$^7$-Arg$^8$-Pro$^9$-D-Ala$^{10}$-NH$_2$, Ac-D-Nal(2)$^1$-D-Cpa$^2$-D-Pal(3)$^3$-Ser$^4$-N-Me-Tyr$^5$-D-Lys(B)$^6$-Nle$^7$-Arg$^8$-Pro$^9$-Sar$^{10}$-NH$_2$, Ac-D-Nal(2)$^1$-D-Cpa$^2$-D-Pal(3)$^3$-Ser$^4$-N-Me-Tyr$^5$-D-Lys(B)$^6$-Nle$^7$-Arg$^8$-Pro$^9$-D-Ala$^{10}$-NH$_2$ and Ac-D-Nal(2)$^1$-D-Cpa$^2$-D-Pal(3)$^3$-Ser$^4$-N-Me-Tyr$^5$-D-Lys(B)$^6$-Nle$^7$-Lys(iPr)$^8$-Pro$^9$-Sar$^{10}$-NH$_2$, and also their salts with the abovementioned pharmaceutically acceptable acids.

The invention provides methods for the treatment of hormone-dependent tumors and hormone-influenced, non-malignant indications which are treatable by LH-RH suppression, comprising administering to a patient in need of such treatment a therapeutically effective amount of a compound according to the invention. As used herein, the term tumor refers to an abnormal growth of tissue, which can be either benign or malignant; i.e., a cancer. The invention provides methods for the treatment of hormone-dependent cancers that include but are not restricted to prostate cancer, breast cancer, ovarian cancer, endometrial cancer, and pancreatic cancer. The invention also provides methods for the treatment of non-malignant indications which are treatable by LH-RH suppression. Such indications which can be treated effectively by the method of the invention include but are not limited to benign prostate hyperplasia (BPH), endometriosis, acne, polycystic ovarian disease, dysmenorrhea, precocious puberty, and uterine fibroids and other leiomyomas.

For practicing the methods for treating hormone-dependent tumors and/or non-malignant indications of the invention, the compounds of the invention are mixed with the customary vehicles and excipients and formulated as medicaments, and are administered using known procedures.

The synthesis of compounds according to formula (I) can both be carried out either by classical fragment condensation or by solid-phase synthesis according to Merrifield with synthesis following one another using D-lysine already acylated in the side chain with the carboxylic acid of the general formula R$^1$—COOH or by reaction of a decapeptide unit with the appropriate carboxylic acids by amide linkage in the side chain of D-lysine$^6$. Accordingly, the introduction of the R$^1$—CO-group can be performed in three different positions in the process: before the condensation of the individual units to give the peptide, after the incorporation of lysine or ornithine in the peptide chain, but before the condensation of the next unit or after condensation of all units.

DETAILED DESCRIPTION OF THE INVENTION

The compounds of the formula (I) are synthesized according to the known methods, such as, for example, by pure solid-phase technique, partly solid-phase technique (so-called fragment condensation) or by the classical solution couplings (see M. Bodanszky, "Principles of Peptide Synthesis", Springer Verlag 1984).

For example, the methods of solid-phase synthesis are described in the textbook "Solid Phase Peptide Synthesis", J. M. Stewart and J. D. Young, Pierce Chem. Company, Rockford, III, 1984, and in G. Barany and R. B. Merrifield "The Peptides", Ch. 1, pp. 1-285, 1979, Academic Press Inc. Classical solution syntheses are described in detail in the treatment "Methoden der Organischen Chemie [Methods of Organic Chemistry] (Houben-Weyl), Synthese von Peptiden" [Synthesis of Peptides] E. Wünsch (Editor) 1974, Georg Thieme Verlag, Stuttgart, FRG.

The stepwise synthesis is carried out, for example, by first covalently bonding the carboxy-terminal amino acid whose α-amino group is protected to an insoluble support which is customary for this, removing the α-amino protective group of this amino acid, bonding the free amino group thus obtained to the next protected amino acid via its carboxyl group, and in this manner linking the customary amino acids of the peptide to be synthesized in the correct sequence step for step, and after linkage of all amino acids removing the finished peptide from the support and removing any further side function protective groups which may be present. The stepwise condensation is carried out in a conventional manner by synthesis from the corresponding, customarily protected amino acids.

The linkage of the individual amino acids to one another is carried out according to the methods cu stomary for this. Suitable methods include:

Symmetrical anhydride method in the presence of dicyclohexylcarbodiimide or diisopropylcarbodiimide (DCC, DIC)

Carbodiimide method generally

Carbodiimide/hydroxybenzotriazole method (see The Peptides, Volume 2, Ed. E. Gross and J. Meienhofer).

Fragment coupling can be effected by the azide coupling method, which proceeds without racemization, or the DCC-1-hydroxybenzotriazole or DCC-3-hydroxy-4-oxo-3,4-dihyro-1,2,3-benzotriazine method. Activated esters of fragments can also be employed.

Esters of N-protected amino acids, such as, for example, N-hydroxysuccinimide esters or 2,4,5- trichlorophenyl esters, are suitable for the stepwise condensation of amino acids. The aminolysis can be catalysed by N-hydroxy compounds which have approximately the acidity of acetic acid, such as, for example, 1-hydroxybenzotriazole.

Intermediate amino protective groups which present themselves are groups which are removed by hydrogenation, such as, for example, the benzyloxycarbonyl radical (=Z radical) or groups which can be removed by weak acid. Suitable protective groups for the α-amino groups are, for example:

tertiary butyloxycarbonyl groups, fluorenylmethyl-oxycarbonyl groups, carbobenzoxy groups or carbobenzothio groups (if appropriate in each case having a p-bromo- or p-nitrobenzyl radical), the trifluoroacetyl group, the phthalyl radical, the o-nitrophenoxyacetyl group, the trityl group, the p-toluenesulphonyl group, the benzyl group, benzyl radicals substituted in the benzene nucleus (p-bromo- or p-nitrobenzyl radical) and the α-phenylethyl radical. Reference is also made here to P. Greenstein and Milton Winitz, Chemistry of Amino Acids, New York 1961, John Wiley and Sons, Inc., Volume 2, for example page 883 et seq., "Principles of Ppetide Synthesis", Springer Verlag 1984, "Solid Phase Peptide Synthesis", J. M. Stewart and J. D. Young, Pierce Chem. Company, Rockford, III, 1984, G. Barany and R. B. Merrifield "The Peptides", Ch. 1, pp. 1-285, 1979, Academic Press Inc., and also The Peptides, Volume 2, Ed. E. Gross and J. Maienhofer, Academic Press, New York. These protective groups are also suitable for the protection of further functional side groups (OH groups, NH$_2$ groups) of the corresponding amino acids.

Hydroxyl groups present (serine, threonine) can be protected by benzyl groups and similar groups. Additional amino groups not in the a-position (for example amino groups in the i-position, guanidino group of arginine) are orthogonally protected.

The individual amino acid units, excluding lysine or ornithine modified by the $R^2$—CO-group, are commercially obtainable. A possible course of the process for the preparation of the latter compounds is as follows:
1. The α-carboxylic acid group is amidated.
2. The ε-amino group is protected by the Z group.
3. The α-amino group is protected by the Boc group such that a selectivity with respect to the later removal of the amino protective groups results.
4. The Z group on the ε-amino group is removed.
5. The desired group $R^4$—CO— is introduced on the ε-amino group.
6. The Boc group on the α-amino group is removed.
7. The α-amino group is provided with the Z group.

For the introduction of the R 2—CO-group by reaction of the amino group of the lysine with appropriate carboxylic acid, suitable processes include the same processes described above for the linkage of the amino acids. Condensation can be effected, for example, using carbQdiimide; e.g. 1-ethyl-3-(3-dimethylamino-propyl)carbodiimide, and 1-hydroxybenzotriazole.

The reaction for the linkage of the amino acids takes place in an inert solvent or suspending agent which is customary for this (for example dichloromethane), it being possible to add dimethylformamide, if necessary, to improve the solubility.

Suitable synthetic supports are insoluble polymers, for example polystyrene resin in bead form, which can be swollen in organic solvents (for example a copolymer of polystyrene and 1% divinylbenzene). The synthesis of a protected decapeptide amide on a methylbenzhydrylamine resin (MBHA resin, i.e. polystyrene resin provided with methylbenzhydrylamine groups), which affords the desired C-terminal amide function of, the peptide after HF cleavage from the support, can be carried out according to the following flow diagram:

Flow Diagram

Peptide Synthesis Protocol

| Stage | Function | Solvent/Reagent (v/v) | Time |
|---|---|---|---|
| 1 | Washing | Methanol | 2 × 2 min |
| 2 | Washing | DCM | 3 × 3 min |
| 3 | Removal | DCM/TFA (1:1) | 1 × 30 min |
| 4 | Washing | Isopropanol | 2 × 2 min |
| 5 | Washing | Methanol | 2 × 2 min |
| 6 | Washing | DCM | 2 × 3 min |
| 7 | Neutralization | DCM/DIPEA (9:1) | 3 × 5 min |
| 8 | Washing | Methanol | 2 × 2 min |
| 9 | Washing | DCM | 3 × 3 min |
| 10 | STOP | Addition of the Boo-As in DCM + DIC + HOBt | |
| 11 | Coupling | DCM, optionally DCM/DCF | approx. 90 min |
| 12 | Washing | Methanol | 3 × 2 min |
| 13 | Washing | DCM | 2 × 3 min |

The Nα-Boc-protected amino acids are customarily coupled in a three fold molar excess in the presence of diisopropylcarbodiimide (DIC) and 1-hydroxybenzo-triazole (HOBt) in $CH_2Cl_2$/DMF in the course of 90 min, and the Boc-protected group is removed by action of 50% trifluoroacetic acid (TFA) in $CH_2Cl_2$ for half an hour. To check for complete conversion, the chloranil test according to Christensen and the Kaiser's ninhydrin test can be used. Radicals of free amino functions are blocked by acetylation in a five fold excess of acetylimidazole in $CH_2Cl_2$. The sequence of the reaction steps of the peptide synthesis on the resin follows from the flow diagram. For the removal of the resin-bound peptides, the respective final product of the solid phase synthesis is dried in vacuo over $P_2O_5$ and treated at 0° C. for 60 min in a 500-fold excess of HF/anisole 10:1/v:v.

After distilling of HF and anisole in vacuo, the peptide amides are obtained as white solids by washing with anhydrous ethyl ether with stirring, and the removal of polymeric support additionally obtained is carried out by washing with 50% strength aqueous acetic acid. By careful concentration of the acetic acid solutions in vacuo, the respective peptides can be obtained as highly viscous oils, which are converted into white solids after addition of abs. ether in the cold.

Further purification is carried out by routine methods of preparative high-pressure liquid chromatography (HPLC).

The conversion of the peptides into their acid addition salts can be effected in a manner known per se by reaction thereof with acids. Conversely, free peptides can be obtained by reaction of their acid addition salts with bases. Peptide embonates can be prepared by reaction of trifluoroacetic acid salts (TFA salts) of the peptide with free embonic acid (pamoic acid) or the corresponding disodium salt of embonic acid. For this, the peptide TFA salt is treated in aqueous solution with the solution of disodium embonate in polar aprotic medium, preferably dimethylacetamide, and the pale yellow precipitate formed is isolated.

Another aspect of the present invention relates to pharmaceutical compositions comprising a compound of the present invention as the active ingredient and a pharmaceutically acceptable carrier. Pharmaceutically acceptable carriers suitable for the pharmaceutical compositions of the invention comprise non-toxic compatible substances useful for preparing a composition for administering the compound to a patient in need of treatment.

Suitable pharmaceutically acceptable carriers generally include, but are not limited to, non-toxic, inert solid, semi-solid, or liquid filler, diluent, encapsulating material or formulation auxiliary of any type. Exemplary material which can serve as pharmaceutically acceptable carriers are sugars, such as lactose, glucose, and sucrose; starches, such as corn starch and potato starch; cellulose and its derivatives, such as sodium carboxymethylcellulose, ethylcellulose and cellulose acetate; powdered tragacanth; malt; gelatin; talc, excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol, and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the pharmaceutically acceptable composition.

The invention provides methods for the treatment of hormone-dependent tumors and hormone-influenced, non-malignant indications which are treatable by LH-RH suppression, comprising administering to a patient in need of such treatment a therapeutically effective amount of a compound as previously defined. Hormone-dependent cancers that can be treated with the methods of the invention include but are not restricted to prostate cancer, breast cancer, ovarian cancer, endometrial cancer, and pancreatic cancer. Non-malignant indications which can be treated by the methods of the invention include but are not limited to benign prostate hyperplasia (BPH), endometriosis, acne, polycystic ovarian disease, dysmenorrhea, precocious puberty, and uterine fibroids and other leiomyomas.

Compounds of the invention are administered to a patient in need of such treatment by any of a variety of routes depending on the specific end use. Generally, the means for administering the peptide to a patient will be a method selected from treatments consisting of oral, parenteral, vaginal, rectal, buccal (including sublingual), transdermal, and intranasal administration. Parental routes of administration include, but are not limited to subcutaneously, intramuscularly, and intravenously. The exact method and route of administration can be determined by one of ordinary skill in the medical arts having knowledge and the ability to develop a reasoned judgment as to the form of treatment administered to the patient in need of treatment.

The exact dose and regimen for administration may depend on a variety of any factors including, but not limited to, the age, size, sex, health, and need of the individual subject being treated, the type of treatment, the degree of affliction or need, and length and frequency of the treatment.

The methods of treatment of the invention comprise administering to a patient a dosage of 65 mg to 900 mg of a peptide LH-RH antagonist of the invention during each of one or more cycles of treatment, each being of from one to 24 weeks in duration. For example, the method of the invention can be practiced with therapeutic effect by administering 65 mg to 300 mg of a compound of the invention to a patient during one or more cycles of treatment of from four to 12 weeks; e.g., during a single four-week cycle, or during each of two, three, or more four-week cycles of treatment.

The methods of the invention are also practiced with therapeutic effect by administering to a patient a dosage of 5 mg to 130 mg of a peptide LH-RH antagonist of the invention during each of one or more cycles of treatment of from one to 24 weeks in duration. For example, hormone-influenced, non-malignant indications such as benign prostate hyperplasia and endometriosis can be treated successfully using this lower range of dosages. In one form of the invention, patients are treated effectively by administering a dosage of 10 mg to 30 mg of a compound of the invention to the patient during one or more cycles of treatment of from four to 12 weeks e.g., during a single four-week cycle, or during each of two, three, or more four-week cycles of treatment. In another effective embodiment of the invention, patients are treated by administering a dosage of 10 mg to 60 mg of a compound of the invention to the patient during each of one or more cycles of treatment of from four to 12 weeks.

The following description of treatment regimens of the invention pertains equally to methods of the invention in which higher dosages, e.g., 65 mg to 300 mg of a peptide LH-RH antagonist of the invention, are administered, and to methods of the invention in which lower higher dosages, e.g., 5 mg to 130 mg of a compound of the invention, are administered. The cycles of treatment of the method can all be the same length of time, e.g., each cycle may be four weeks long. Alternatively, two or more cycles may extend over different time periods. The total amount of the LH-RH antagonist of the invention that is administered can be the same in each cycle, or different amounts can be administered in different cycles. For a given cycle, the LH-RH antagonist of the invention can be administered in any dosage regimen that provides therapeutic benefit to the patient. For example, the compound of the invention can be administered as a single dose during the treatment cycle, as two equal doses on days 1 and 2 of the treatment cycle, two equal doses on days 1 and 8 of the treatment cycle, two equal doses on days 1 and 15 of the treatment cycle, more than two equal or unequal doses, a weekly dose, or a daily dose; e.g., as a series of daily doses given over the course of the treatment cycle. The dosage regimen by which the compound of the invention is administered can be the same in each cycle, it can vary between any two cycles, or can be different for each cycle. For example, repetitive treatments given in successive cycles can be performed with varying doses; e.g., 100 mg can be administered on day 1, 65 mg on day 29, 65 mg on day 57, and so on. A single dose can consist of from 65 mg to 300 mg or more of the compound of the invention. For example, a single dose can consist of (but is not limited to) 65 mg, 80 mg, 100 mg, 120 mg, 130 mg, 180 mg, 200 mg, 240 mg, or 300 mg of the compound. Alternatively, depending on the disease or disorder being treated and the condition of the patient, a single dose can consist of (but is not limited to) 5 mg, 10 mg, 15 mg, 20 mg, or 30 mg of the compound. The treatment can be carried out chronically or as an intermitted treatment with treatment-free periods of 1-12 months, in between treatment cycles. For example, patients can be treated effectively by the method of the invention wherein the treatment is carried out as an intermitted treatment with treatment-free periods between treatment cycles of duration selected from the group consisting of 3, 6, 9, and 12 months. The time period of the treatment cycles, the number of cycles, the dosage administered during each cycle, and the regimen by which the compound of the invention is administered to provide therapeutic benefit to the patient are determined by routine methods.

The following examples serve to illustrate the invention without restricting it.

EXAMPLE 1

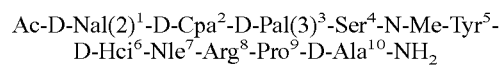

Ac-D-Nal(2)$^1$-D-Cpa$^2$-D-Pal(3)$^3$-Ser$^4$-N-Me-Tyr$^5$-D-Hci$^6$-Nle$^7$-Arg$^8$-Pro$^9$-D-Ala$^{10}$-NH$_2$

The synthesis was carried out according to a solid-phase flow diagram (Peptide Synthesis Protocol, p. 11) with DIC/HOBt coupling, starting from 3.3 g of MBHA resin (loading density 1.08 mmol/g). After HF cleavage from the polymeric support, 3.4 g of crude peptide were obtained, which were purified by standard processes of preparative HPLC. After subsequent freeze-drying, 1.43 g of HPLC-uniform product of the empirical formula $C_{72}H_{96}N_{17}O_{14}Cl$ having correct FAB-MS: 1458.7 (M+H$^+$) (calc: 1457.7), and corresponding $^1$H-NMR spectrum were obtained.

$^1$H-NMR (500 MHz, D$_2$0/DMSO-d$_6$, δ in ppm): 8.7 to 7.2, several m, arom. H and incompletely exchanged NH; 6.92 and 6.58, 2d, 2×2H, arom. H p-Cl-Phe; 5.2 to 3.5, several m, Cα-H and aliph. H; 3.2 to 2.6, several m, aromat. Cβ-H 2.1 to 0.7, several m, residual aliphat. H; 1.70, s, 3H, acetyl; 1.20, d, 3H, Cβ-H Ala; 0.8, m, Cδ-H Leu

EXAMPLE 2

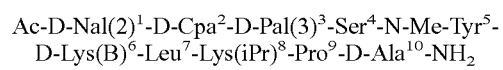

Ac-D-Nal(2)$^1$-D-Cpa$^2$-D-Pal(3)$^3$-Ser$^4$-N-Me-Tyr$^5$-D-Lys(B)$^6$-Leu$^7$-Lys(iPr)$^8$-Pro$^9$-D-Ala$^{10}$-NH$_2$

The synthesis was carried out according to a flow diagram (Peptide Synthesis Protocol, p. 11) with DIC/HOBt coupling, starting from 4.0 g of MBHA resin (loading density 1.11 mmol/g). After HF cleavage from the polymeric support, 4.87 g of crude peptide were obtained, which were purified by standard processes of preparative HPLC. After subsequent freeze-drying, 0.93 g of HPLC-uniform product was obtained, which was reacted with 4-amidinophenylamino-4-oxobutyric acid in the presence of BOP as a coupling reagent to give the desired compound. After fresh HPLC purification, 148 mg of target compound of the empirical formula $C_{85}H_{112}N_{17}O_{15}$—Cl having correct ESI-MS: 1647.6 (N+H$^+$) (calc: 1645.8), and corresponding $^1$H-NMR spectrum were obtained.

$^1$H-NMR (500 MHz, DMSO-d$_6$, δ in ppm): 10.4, s, 1H and 9.13, s, 2H, and 8.94, s, 2H, NHs of 4-amidinoaniline; 8.6 to 7.35, several m, arom. H and NH; 7.22 and 7.18, 2d, 4H, arom. H (pCl)Phe; 6.95 and 6.58, 2d, 4H, arom. H Tyr; 5.2 to 3.5, several m, Cα-H and aliphat. H; 3.3 to 2.4, several m, Cβ-H and N—CH$_3$; 2.1 to 1.1, several m, residual aliphat. H; 1.68, s, 3H, acetyl; 1.20, d, 3H, Cβ-H, Ala; 0.83, dd, 6H, Cδ-H Leu

EXAMPLE 3

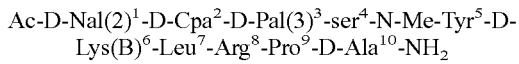

Ac-D-Nal(2)$^1$-D-Cpa$^2$-D-Pal(3)$^3$-ser$^4$-N-Me-Tyr$^5$-D-Lys(B)$^6$-Leu$^7$-Arg$^8$-Pro$^9$-D-Ala$^{10}$-NH$_2$ The synthesis was carried out according to a solid-phase flow diagram (Peptide Synthesis Protocol, p. 11) with DIC/HOBt coupling, starting from 4.0 g of MBHA resin (loading density 0.97 mmol/g). After HF cleavage from the polymeric support, 4.0 g of crude peptide were obtained, which were purified by standard processes of preparative HPLC. After subsequent freeze-drying, 1.39 g of HPLC-uniform product were obtained, which were reacted with 4-amidinophenylamino-4-oxobutyric acid in the presence of BOP as a coupling reagent to give the desired compound. After fresh HPLC purification, 440 mg of target compound of the empirical formula $C_{82}H_{106}N_{19}O_{15}$Cl having correct ESI-MS: 1632.7 (M+H$^+$) (calc: 1631.7), and corresponding $^1$H-NMR spectrum were obtained.

$^1$H-NMR {500 MHz, DMSO-d$_6$ δ in ppm): 10.4, s, 1H and 9.15, s, 2H, and 9.0, s, 2H, NHs of 4-amidinoaniline; 8.60, m, 2H, arom. H; 8.3 to 7.2, several m, arom. H and NH; 7.27 and 7.20, 2d, 4H, arom. H (pCl) Phe; 6.96 and 6.60, 2d, 4H, arom. H Tyr; 5.2 to 3.5, several m, Cβ-H and aliphat. H; 3.2 to 2.4, several m, Cβ-H and N—CH$_3$; 2.1 to 1.1, several m, residual aliphat. H; 1.70, s, 3H, acetyl; 1.20, d, 3H, Cβ-H Ala; 0.85, dd, 6H, Cδ-H Leu

EXAMPLE 4

Ac-D-Nal(2)$^1$-D-Cpa$^2$-D-Pal(3)$^3$-Ser$^4$-N-Me-Tyr$^5$-D-Hci$^6$-Nle$^7$-Lys(iPr)$^8$-Pro$^9$-D-Ala$^{10}$-NH$_2$

The synthesis was carried out according to a solid-phase flow diagram (Peptide Synthesis Protocol, p. 11) with DIC/HOBt coupling, starting from 2.5 g of MBHA resin (loading density 1.08 mmol/g). After HF cleavage from the polymeric support, 2.78 g of crude peptide were obtained, which were purified by standard processes of preparative HPLC. After subsequent freeze-drying, 400 mg of HPLC-uniform product of the empirical formula $C_{75}H_{102}N_{15}O_{14}$Cl having correct ESI-MS: 1472.6 (M+H$^+$) (calc: 1471.7), and corresponding $^1$H-NMR spectrum were obtained.

$^1$H-NMR (500 MHz, D$_2$0/DMSO-d$_6$, δ in ppm): 8.62, m, 2H, 8.30, m, 2H, 7.80, m, 4H, 7.66, s, 1H, 7.47, m, 2H, 7.36, d, 1H, aromat. H; 7.25 and 7.20, 2 d, 4H, arom. H (pCl)Phe; 6.96 and 6.63, 2d, 4H, aromat. H Tyr; 5.10 to 4.0, several m, Cα-H and aliphat. H; 3.75 to 2.65, several m, Cβ-H and N—CH3; 2.1 to 1.05, several m, residual aliphat. H; 1.74, s, 3H, acetyl; 1.23, d, 3H, Cβ-H Ala; 1.20, m, CH$_3$ isoprop.; 0.8, m, 3H, Cδ-H Nle

EXAMPLE 5

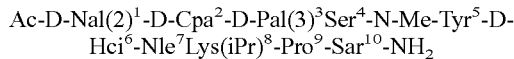

Ac-D-Nal(2)$^1$-D-Cpa$^2$-D-Pal(3)$^3$Ser$^4$-N-Me-Tyr$^5$-D-Hci$^6$-Nle$^7$Lys(iPr)$^8$-Pro$^9$-Sar$^{10}$-NH$_2$

The synthesis was carried out according to a solid-phase flow diagram (Peptide Synthesis Protocol, p. 11) with DIC/HOBt coupling, starting from 2.5 g of MBHA resin (loading density 1.08 mmol/g). After HF cleavage from the polymeric support, 2.74 g of crude peptide were obtained, which were purified by standard processes of preparative HPLC. After subsequent freeze-drying, 840 mg of HPLC-uniform product of the empirical formula $C_{75}H_{102}N_{15}O_{14}$Cl having correct ESI-MS: 1472.6 (M+H$^+$) (calc: 1471.7), and corresponding $^1$H-NMR spectrum were obtained.

$^1$H-NMR (500 MHz, D$_2$0/DMSO-d$_6$, δ in ppm): 8.6, m, 2H, 8.3, m, 2H, 7.85, m, 2H, 7.8, m, 2H, 7.65, s, 1H, 7.46, m, 2H, 7.35, d, 1H, aromat. H; 7.23 and 7.17, 2 d, 4H, arom. H (pCl)Phe; 7.0 and 6.6, 2d, 4H, aromat. H Tyr; 5.10 to 3.8, several in, Cα-H and aliphat. H; 3.75 to 2.6, several m, Cβ-H and N—CH$_3$; 2.2 to 1.05, several m, residual aliphat. H; 1.70, s, 3H, acetyl; 1.23, d, 3H, Cβ-H Ala; 1.20, m, CH$_3$ isoprop.; 0.8, m, 3H, Cδ-H Nle

EXAMPLE 6

3-(4-Fluorophenyl)propionyl-D-Nal(1)$^1$-Ser$^4$-N-Me-Tyr$^5$-D-Lys (Atz)$^6$-Leu$^7$-Arg$^8$-Pro$^9$-D-Ala$^{10}$-NH$_2$ The synthesis was carried out according to a solid-phase, flow diagram (Peptide Synthesis Protocol, p. 11) with DIC/HOBt coupling, starting from 9.2 g of MBHA resin (loading density 1.08 mmol/g). After HF cleavage from the polymeric support, 5.8 g of crude peptide were obtained, which were purified by standard processes of preparative HPLC. After subsequent freeze-drying, 2.0 g of HPLC-uniform unsubstituted octapeptide were obtained, of which 0.4 mmol was reacted with 0.5 mmol of 3-amino-1,2,4-trizole-5-carboxylic acid in the presence of PyBOP as a coupling reagent to give 790 mg of crude product of the desired compound. After fresh HPLC purification, 200 mg of target compound of the empirical formula $C_{64}H_{86}N_{17}O_{12}$F having correct FAB-MS: 1304.6 (M+H$^+$) (calc: 1303.6) were obtained.

$^1$H-NMR (500 MHz, D$_2$0/DMSO-d$_6$, δ in ppm) 8.14, m, 1H, 7.90, m, 1H, 7.80, m, 1H, 7.50, m, 2H, 7.35, m, 2H, 7.0, m, 6H, 7.63, m, 2H, aromat. H; 5.0, m, 1H, 4.83, m, 2H, 4.41, m, 1H, 4.30-4.05, several m, 4H, Cα-H; 3.66 to 2.25, several m, aliphat. and aromat. side-chain H; 2.95, s, and 2.75, s, N—Me; 2.05 to 1.1, several m, residual aliphat. H; 1.20, d, Cβ-H Ala; 0.75, m, 6H, Cδ-H Leu

EXAMPLE 7

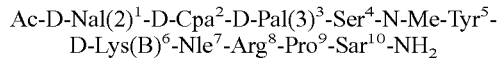

Ac-D-Nal(2)$^1$-D-Cpa$^2$-D-Pal(3)$^3$-Ser$^4$-N-Me-Tyr$^5$-D-Lys(B)$^6$-Nle$^7$-Arg$^8$-Pro$^9$-Sar$^{10}$-NH$_2$

The synthesis of the decapeptide was carried out on a polymeric support with a loading density of 0.55 mmol/g (aminomethyl-substituted resin, Fmoc protection, Type D-1675, Bachem). Lysine was coupled as Fmoc-D-Lys(Boc)-OH, and the Fmoc protective groups were removed using 20% piperidine/DMF. After simultaneous removal of all side-chain protective groups and detachment from the polymeric support, the isolated crude peptide was purified by means of preparative HPLC. After freeze-drying, 98.5% pure decapeptide was obtained.

The substitution on the ε nitrogen of D-lysine with 4-(4-aminophenol)amino-1,4-dioxobutyric acid was carried out using PyBop in DMF with addition of DIPEA. The purification of the isolated crude peptide was carried out by means of preparative HPLC. The subsequent freeze-drying afforded about 99% pure product (trifluoroacetate) of the empirical formula C82 H106 Cl N19 O15 having correct FAB-MS of 1632 (M+H) (calc: 1631.78096)

EXAMPLE 8

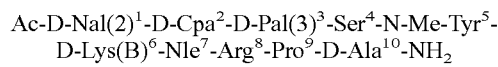

The synthesis of the decapeptide was carried out on a polymeric support with a loading density of 0.55 mmol/g (aminomethyl-substituted resin, Fmoc protection, Type D-1675, Bachem). Lysine was coupled as Fmoc-D-Lys(Boc)-OH, and the Fmoc protective groups were removed using 20% piperidine/DMF. After simultaneous removal of all side-chain protective groups and detachment from the polymeric support, the isolated crude peptide with a purity of about 71% (HPLC) was reacted further without purification.

The side-chain substitution of D-lysine with 4-(4-aminophenol)amino-1,4-dioxobutyric acid was carried out using PyBop in DMF with addition of DIPEA. The isolated crude peptide was purified by means of preparative HPLC. After subsequent freeze-drying, a 98.8% pure product (trifluoroacetate) of the empirical formula $C_{82}H_{106}ClN_{19}O_{15}$ having correct FAB-MS of 1632 (M+H) (calc: 1631.78096) was obtained.

EXAMPLE 9

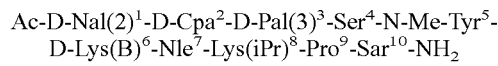

The synthesis of the decapeptide was carried out on a polymeric support with a loading density of 0.55 mmol/g (aminomethyl-substituted resin, Fmoc protection, Type D-1675, Bachem). Lysine was coupled as Fmoc-D-Lys(Boc)-OH, and the Fmoc protective groups were removed using 20% piperidine/DMF. After simultaneous removal of all side-chain protective groups and detachment from the polymeric support, the isolated crude peptide (concentration about 59%, HPLC) was purified by means of preparative HPLC. After freeze-drying, 95% pure decapeptide was obtained.

The side-chain substitution of D-lysine with 4-(4-aminophenol)amino-1,4-dioxobutyric acid was carried out using PyBop in DMF with addition of DIPEA. The isolated crude peptide was purified by means of preparative HPLC. After subsequent freeze-drying, a 96.6% pure product (trifluoroacetate) of the empirical formula $C_{85}H_{112}ClN_{17}O_{15}$ having correct FAB-MS of 1646 (M+H) (calc: 1645.8218) was obtained.

EXAMPLE 10

The compounds according to the invention can be tested o determine their binding affinities for LH-RH receptor and their functional activities as LH-RH antagonists using the following methods, Methods 1 and 2.

Method 1.

The compounds according to formula I of the invention were investigated for their receptor binding. The assay method closely followed the process described in Beckers et al., "Selection and characterization of mammalian cell lines with stable overexpression of human pituitary receptors for gonadoliberin (GnRH)" (1995) Eur. J. Biochem., 231, 535-543. Cetrorelix obtained according to the synthesis disclosed above was iodinated with [$^{125}$I] (Amersham; specific activity 80.5 Bq/fmol) using the IodoGen reagent (Pierce). The reaction mixture was purified by reverse-phase high-performance liquid chromatography with exchanged phases, monoiodinated cetrorelix being obtained without unlabelled peptide. In each case, about 80% of the [$^{125}$I]-cetrorelix was capable of specific receptor association.

The receptor binding assay was carried out under physiological conditions as described (Beckers et al., 1995) using intact cells. Subconfluent cultures of stably transfected LTK cells, which express the human LHRH receptor, were separated off by incubation in NaCl/P$_i$ (137 mM NaCl, 2.7 mM KCl, 8.1 mM Na$_2$HPO$_4$, 11.47 mM KH$_2$PO$_4$)/1 mM EDTA and collected by centrifugation. The cell pellet was resuspended in binding buffer (DMEM without H$_2$CO$_3$, with 4.5 g/l of glucose, 10 mM Hepes pH 7.5, 0.5% (mass/volume) BSA, 1 g/l bacitracin, 0.1 g/l SBTI, 0.1% (mass/volume) NaN$_3$). For displacement assays, 0.25×10$^6$ cells/100 µl were incubated with approximately 225 pM of the [$^{125}$I]-cetrorelix (specific activity 5-10×10$^5$ dpm/pmol) and various concentrations of unlabelled compound according to the invention as competitor. The cell suspension in 100 µl of binding medium was layered in 400 µl assay tubes over 200 µl of 84% by volume silicone oil (Merck Type 550)/16% by volume paraffin oil. After incubation for 1 h at 37° C. with slow, continuous shaking, the cells were separated from the incubation medium by centrifugation for 2 min at 9000 rpm (rotor type HTA13.8; Heraeus Sepatec, Osterode/Germany). The tips of the tubes which contained the cell pellet were cut off. Cell pellet and supernatants were then analysed by counting the γ radiation. The amount of non-specifically bound material was determined at a final concentration of 1 µM with inclusion of unlabelled cetrorelix and was typically ≦10% of the total bound material. The analysis of the binding data was carried out using the EBDA/ligand analysis programme (Biosoft V3.0).

Method 2.

Functional Assay for the Determination of the Antagonistic Activity

The assay for the functional characterization of antagonistic analogs of LH-RH was carried out, with some modifications, as described in Beckers et al., "Characterization of gonadotropin-releasing hormone analogs based on a sensitive cellular luciferase reporter gene assay" (1997) Analyt. Biochem. 251, 17-23. The assay uses a reporter gene made by fusing the c-fos immediate-early gene promoter to a DNA sequence encoding luciferase (Luc). A recombinant cell line that expresses the human LH-RH. receptor is stably transfected with the fos-Luc reporter gene. Transcription of the fos-Luc fusion gene and synthesis of the Luc protein is induced in the cells in a dose-dependent manner by LH-RH and other LH-RH agonists that bind and signal through the human LH-RH receptor. Peptide LH-RH antagonists such as the compounds of the invention bind to cellular LH-RH receptors and inhibit this stimulation. The antagonistic potency (IC50) of peptide LH-RH antagonists as determined by the assay generally correlates well with the binding affinity (KD) of the LH-RH antagonists for LH-RH receptor as determined from ligand binding experiments.

Cells containing the fos-Luc reporter gene that express the human LH-RH receptor were cultured for 24 h in microtitre plates using DMEM with additives and 1% (v:v) FCS (10,000 cells per well). The cells were then stimulated with 1 nM [D-Trp$^6$] LHRH for 6 h. Peptide LH-RH antagonist compounds according to the invention were added before the stimulation, and the cells were lysed at the end for quantification of the cellular Luc activity. The calculation of the IC$_{50}$ values from dose-effect curves was carried out by non-linear regression analysis using the Hill model (Programme EDX 2.0 from C. Grunwald, Arzneimittelwerk Dresden).

The quantification of the Luc activity was carried out in duplicate essentially as described (Promega Technical Bulletins #101/161) using the respective luciferase assay system (Promega E4030). Owing to addition of coenzyme A (CoA), an oxidation of luciferyl-CoA takes place with advantageous kinetics. After the removal of the culture medium from the microtitre plate, the cells were lysed by addition of 100 μl of lysis buffer (25 mM tris-phosphate pH 7.8, 2 mM dithiothreitol, 2 mM 1,2-diaminocyclohexane-N,N,N',N'-tetraacetic acid (CDTA), 10% (v:v) glycerol, 1% (v:v) Triton X-100). After incubation at room temperature for 15 min, 10 μl of cell lysate were transferred into a white microtitre plate suitable for luminometric detection (Dynatech). The enzymatic reaction was initiated by addition of 50 μl of assay buffer (20 mM tricine pH 7.8, 1.07 mM (MgCO$_3$)$_4$Mg(OH)$_2$, 2.67 mM MgSO$_4$, 0.1 mM ethylene-diaminetetraacetic acid (EDTA), 33.3 mM dithiothreitol, 270 μM coenzyme A, 470 μM glow-worm (Photinus pyralis) luciferin, 530 μM rATPNa$_2$). After one minute, the luminescence was determined for a total time of one second with a signal half-life of five minutes using the EG&G Berthold MicroLumat LB 96 P.

In this way, the following in-vitro data were obtained, K$_D$ being the binding affinities and IC$_{50}$ being the functional activity, in units of picomoles per litre (pM):

TABLE 1

| Compound | K$_D$ [pM] | IC$_{50}$ [pM] |
| --- | --- | --- |
| cetrorelix | 170 (21) | 198 (5) |
| Example 1 (Acetate salt) | n.d. | 242 (3) |
| Example 2 | 181 (1) | 684 (2) |
| Example 3 | 154 (1) | 492 (2) |
| Example 6 | n.d. | 221 (2) |
| Example 7 | n.d. | 1300 (1) |
| Example 8 | n.d. | 1400 (1) |
| Example 9 | n.d. | 4700 (1) | n.d. = not determined
( ) = number of independent experiments

EXAMPLE 11

Treatment of Prostate Carcinoma

The following data are derived from two clinical studies comprising 14 and 13 patients, respectively, who suffer from prostate carcinoma and who were treated with the compound of the invention having the formula:

Ac-D-Nal(2)$^1$-D-Cpa$^2$-D-Pal(3)$^3$-Ser$^4$-N-Me-Tyr$^5$-D-Hci$^6$-Nle$^7$-Arg$^8$-Pro$^9$-D-Ala$^{10}$-NH$_2$ (Ozarelix)

In the first clinical trial, patients were given i.m. injections of 65 mg Ozarelix on day 1 followed by another 65 mg i.m. injection on day 2. Patients were re-treated after a waiting period of 4 weeks. This 4 week period of treatment is referred to as a treatment "cycle". Accordingly, dosage of 130 mg of Ozarelix was provided to the patients in the first four week cycle of treatment (Cycle 1).

Six out of these 14 patients were subsequently administered 65 mg Ozarelix per i.m. injection on day 29 and day 30 each, whereas the other eight patients only received 65 mg Ozarelix on day 29 (Cycle 2). This schedule was repeated on day 57/58 accordingly (Cycle 3).

Table 2 shows the mean testosterone values for the 14 patients treated measured at the days indicated. As for the administration days, testosterone levels were always determined before application of ozarelix to the patients. In addition, mean change of Prostate Specific Antigen (PSA) levels were monitored 4-weekly over a period of 12 weeks. The percent change of PSA shown is the mean value for all treated patients and refers to the normalized individual baseline PSA levels before first Ozarelix administration.

TABLE 2

| Day | Testosterone [ng/mL] | PSA [% change] |
| --- | --- | --- |
| 1 (pre-dose) | 4.4 | Start |
| 2 | 0.6 | |
| 3 | 0.3 | |
| 8 | 0.2 | |
| 15 | 0.1 | |
| 22 | 0.1 | |
| 29 | 0.2 | −77 |
| 36 | 0.1 | |
| 43 | 0.1 | |
| 50 | 0.1 | |
| 57 | 0.1 | −88 |
| 64 | 0.1 | |
| 71 | 0.1 | |
| 78 | 0.1 | |
| 85 | 0.3 | −89 |

The data demonstrate an (almost) immediate testosterone castration (<0.5 ng/mL), with 57% of the treated patients being hormonally castrated on day 2 (24 hours post-dose) and 79% being castrated on day 3 (48 hours post-dose). Afterwards, all patients did show testosterone values of below 0.5 ng/mL and a lasting testosterone castration. This ability of Ozarelix to effect essentially immediate hormonal castration was unexpected, and provides an advantage of over other known treatments.

In addition, PSA levels are significantly reduced over the monitoring period, demonstrating the efficacy of Ozarelix inthe treatment of prostate cancer.

In the second clinical trial patients were given a single im. injection of 130 mg Ozarelix on day 1. Patients were re-treated after a waiting period of 4 weeks, and this 4 week period is considered as a treatment "Cycle". Accordingly, dosage of 130 mg of Ozarelix was again provided to the patients in the first four week cycle of treatment (Cycle 1).

Seven out of these 13 patients were subsequently administered 130 mg Ozarelix per i.m. injection on day 29, whereas the other six patients received 100 mg Ozarelix on day 29 (Cycle 2). This schedule was repeated on day 57 accordingly (Cycle 3).

Table 3 shows the mean testosterone values for the 13 patients treated measured at the days indicated. As for the administration days, testosterone levels were always determined before application of Ozarelix to the patients.

TABLE 3

| Day | Testosterone [ng/mL] |
| --- | --- |
| 1 (pre-dose) | 3.9 |
| 2 | 0.4 |

TABLE 3-continued

| Day | Testosterone [ng/mL] |
|---|---|
| 3 | 0.3 |
| 8 | 0.1 |
| 15 | 0.1 |
| 22 | 0.1 |
| 29 | 0.2 |
| 36 | 0.1 |
| 43 | 0.1 |
| 50 | 0.1 |
| 57 | 0.2 |
| 64 | 0.1 |
| 71 | 0.1 |
| 78 | 0.1 |
| 85 | 0.3 |

The data again demonstrate an (almost) immediate testosterone castration (<0.5 ng/mL), with 69% of the treated patients being hormonally castrated on day 2 (24 hours post-dose) and 100% being castrated on day 3 (48 hours post-dose). Afterwards, all patients continued to show testosterone values of below 0.5 ng/mL and a lasting testosterone castration. As noted above, the almost immediate hormonal castration effected by Ozarelix was unexpected, and represents an advantage of the use of Ozarelix over competitive treatments.

EXAMPLE 12

Treatment of Benign Prostate Hyperplasia (BPH)

In a placebo-controlled clinical trial (still running) 144 patients who suffer from BPH are either treated with Ozarelix or a placebo.

In a first treatment group, 27 patients are given i.m. injections of 5 mg Ozarelix on Day 1 followed by another 5 mg i.m. injection on Day 15 in a period of 4 weeks (treatment "cycle"). In a second treatment group, 27 patients are given i.m. injections of 10 mg Ozarelix on Day 1 followed by another 10 mg i.m. injection on Day 15 in a period of 4 weeks (treatment "cycle"). In a third treatment group, 27 patients are given i.m. injections of 20 mg Ozarelix on Day 1 in a period of 4 weeks (treatment "cycle") In a fourth treatment group, 27 patients are given i.m. injections of 15 mg Ozarelix on Day 1 followed by another 15 mg i.m. injection on Day 15 in a period of 4 weeks (treatment "cycle").

Accordingly, the dosing amounts to 10 mg, 20 mg, 20 mg and 30 mg, respectively, per four weeks (treatment cycle).

Following that 4-weeks treatment cycle patients are not treated for a period of 2 to 12 months, preferably 3 to 6 months. Afterwards a new 4-weeks treatment cycle is started (intermitted treatment).

Alternatively, the 4-weeks treatment cycle may be repeated 1 to 6 times, preferably 1 to 3 times before patients enter the treatment-free period of 2 to 12 months, preferably 3 to 6 months.

EXAMPLE 13

Treatment of Endometriosis

In a placebo-controlled clinical trial (planned) female patients who suffer from endometriosis are either treated with Ozarelix or a placebo.

In a first treatment group, 27 patients are given i.m. injections of 5 mg Ozarelix on Day 1 followed by another 5 mg i.m. injection on Day 15 in a period of 4 weeks (treatment "cycle"). In a second treatment group, 27 patients are given i.m. injections of 10 mg Ozarelix on Day 1 followed by another 10 mg i.m. injection on Day 15 in a period of 4 weeks (treatment "cycle"). In a third treatment group, 27 patients are given i.m. injections of 20 mg Ozarelix on Day 1 in a period of 4 weeks (treatment "cycle"). In a fourth treatment group, 27 patients are given i.m. injections of 15 mg Ozarelix on Day 1 followed by another 15 mg i.m. injection on Day 15 in a period of 4 weeks (treatment "cycle").

Accordingly, the dosing amounts to 10 mg, 20 mg, 20 mg and 30 mg, respectively, per four weeks (treatment cycle).

Following that 4-weeks treatment cycle patients are not treated for a period of 2 to 12 months, preferably 3 to 6 months. Afterwards a new 4-weeks treatment cycle is started (intermitted treatment).

Alternatively, the 4-weeks treatment cycle may be repeated 1 to 6 times, preferably 1 to 3 times before patients enter the treatment-free period of 2 to 12 months, preferably 3 to 6 months.

Furthermore, above Ozarelix injections may be administered weekly, i.e. on Day 1, Day 8, Day 15 and Day 22 of each treatment cycle with the treatment cycle repeated 1 to 6 times, preferably 1 to 3 times, before patients enter the treatment-free period of 2 to 12 months, preferably 3 to 6 months.

What is claimed is:

1. A method of treating a hormone-influenced non-malignant disorder that is treatable by luteinizing hormone-releasing hormone (LH-RH) suppression, the method comprising administering to a patient in need of the treatment a therapeutically effective amount of a compound of the general formula I

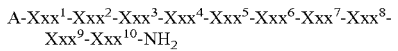
(I)

in which:
A is an acetyl or a 3-(4-fluorophenyl)propionyl group,
$Xxx^1$ is D-Nal(1) or D-Nal(2),
$Xxx^2$-$Xxx^3$ is D-Cpa-D-Pal,(3) or a single bond,
$Xxx^4$ is Ser,
$Xxx^5$ is N-Me-Tyr,
$Xxx^6$ is D-Cit, D-Hci or a D-amino acid group of the general formula II

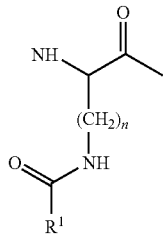
(II)

in which n is the number 3 or 4, where $R^1$ is a group having the general formula III

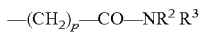
(III)

where p is an integer from 1 to 4, $R^2$ is hydrogen or an alkyl group and $R^3$ is an unsubstituted or substituted aryl group or heteroaryl group, or $R^1$ is a 3-amino-1,2,4-triazole-5-carbonyl group or $R^1$ is a ring of the general formula IV

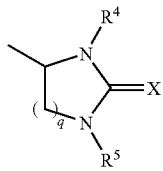
(IV)

in which q is the number 1 or 2, $R^4$ is a hydrogen atom or an alkyl group, $R^5$ is a hydrogen atom or an alkyl group and X is an oxygen or sulphur atom, $Xxx^7$ is Leu or Nle, $Xxx^8$ is Arg or Lys(iPr), $Xxx^9$ is Pro, and $Xxx^{10}$ is Ala, D-Ala, or Sar, and their salts with pharmaceutically acceptable acids.

2. The method of claim 1, in which the salt is an acetate, trifluoroacetate or embonate.

3. The method of claim 1, comprising administering a compound having the formula: Ac-D-Nal(2)$^1$-D-Cpa$^2$-D-Pal(3)$^3$-Ser$^4$-N-Me-Tyr$^5$-D-Hci$^6$-Nle$^7$-Arg$^8$-Pro$^9$-D-Ala$^{10}$-NH$_2$.

4. The method of claim 1, comprising administering a compound having the formula: Ac-D-Nal(2)$^1$-D-Cpa$^2$-D-Pal(3)$^3$-Ser$^4$-N-Me-Tyr$^5$-D-Hci$^6$-Nle$^7$-Lys(iPr)$^8$-Pro$^9$-D-Ala$^{10}$-NH$_2$.

5. The method of claim 1, comprising administering a compound having the formula: Ac-D-Nal(2)$^1$-D-Cpa$^2$-D-Pal(3)$^3$-Ser$^4$-N-Me-Tyr$^5$-D-Hci$^6$-Nle$^7$- Lys(iPr)$^8$-Pro$^9$-Sar$^{10}$-NH$_2$.

6. The method of claim 1, comprising administering a compound having the formula: Ac-D-Nal(2)$^1$-D-Cpa$^2$-D-Pal(3)$^3$-Ser$^4$-N-Me-Tyr$^5$-D-Hci$^6$-Nle$^7$-Arg$^8$-Pro$^9$-Sar$^{10}$-NH$_2$.

7. The method of claim 1 wherein the hormone-influenced non-malignant disorder is selected from the group consisting of benign prostate hyperplasia and endometriosis.

8. A method of treating a hormone-influenced non-malignant disorder that is treatable by LH-RH suppression selected from the group consisting of benign prostate hyperplasia and endometriosis, the method comprising administering to a patient in need of the treatment a therapeutically effective amount of a compound having the formula: Ac-D-Nal(2)$^1$-D-Cpa$^2$-D-Pal(3)$^3$-Ser$^4$-N-Me-Tyr$^5$-D-Hci$^6$-Nle$^7$-Arg$^8$-Pro$^9$-D-Ala$^{10}$-NH$_2$.

* * * * *